United States Patent
Maeda (10) Patent No.: US 9,029,754 B2
(45) Date of Patent: May 12, 2015

(54) LIGHT DETECTION APPARATUS TO INCLUDE AN EXPOSURE TIME PERIOD DETERMINATION UNIT CONFIGURED TO DETERMINE A NOISE LEVEL BASE ON FIRST DARK CURRENT AND SECOND DARK CURRENT

(71) Applicant: Sony Corporation, Tokyo (JP)

(72) Inventor: Tatsuo Maeda, Kanagawa (JP)

(73) Assignee: Sony Corporation, Tokyo (JP)

( * ) Notice: Subject to any disclaimer, the term of this patent is extended or adjusted under 35 U.S.C. 154(b) by 209 days.

(21) Appl. No.: 13/689,066

(22) Filed: Nov. 29, 2012

(65) Prior Publication Data

US 2013/0146750 A1 Jun. 13, 2013

(30) Foreign Application Priority Data

Dec. 9, 2011 (JP) .................... 2011-270584

(51) Int. Cl.
| | | |
|---|---|---|
| *H01L 27/00* | (2006.01) | |
| *H01J 40/14* | (2006.01) | |
| *H01L 27/146* | (2006.01) | |
| *H04N 5/235* | (2006.01) | |
| *G01N 21/64* | (2006.01) | |

(52) U.S. Cl.
CPC ........ *H01L 27/14601* (2013.01); *H04N 5/2351* (2013.01); *H04N 5/2354* (2013.01); *G01N 21/6458* (2013.01)

(58) Field of Classification Search
CPC ...... A61B 1/00; A61B 17/00; A61B 2217/00; A61B 2218/00
USPC ........ 250/208.1, 214.1, 214 R; 348/243, 244, 348/362–366, 295–296; 257/294, 431–435, 257/440; 396/69, 89, 96, 161
See application file for complete search history.

(56) References Cited

U.S. PATENT DOCUMENTS

2007/0222983 A1* 9/2007 Tomaney et al. ............. 356/307

FOREIGN PATENT DOCUMENTS

| JP | 2006349574 | * | 6/2005 |
|---|---|---|---|
| JP | 2009-128648 | | 6/2009 |

* cited by examiner

*Primary Examiner* — Que T Le
*Assistant Examiner* — Don Williams
(74) *Attorney, Agent, or Firm* — K&L Gates LLP (57) ABSTRACT

A light detection apparatus includes an image sensor, a signal obtaining unit, an exposure-time-period determination unit, and an exposure controller. The signal obtaining unit is configured to obtain a first dark current being a dark current of the image sensor in a first exposure time period, and a second dark current being a dark current of the image sensor in a second exposure time period. The exposure-time-period determination unit is configured to determine an optimal exposure time period of the image sensor based on the first dark current and the second dark current. The exposure controller is configured to control the image sensor to be exposed to light for the optimal exposure time period.

7 Claims, 6 Drawing Sheets

LIGHT DETECTION APPARATUS TO INCLUDE AN EXPOSURE TIME PERIOD DETERMINATION UNIT CONFIGURED TO DETERMINE A NOISE LEVEL BASE ON FIRST DARK CURRENT AND SECOND DARK CURRENT

CROSS REFERENCES TO RELATED APPLICATIONS

The present application claims priority to Japanese Priority Patent Application JP 2011-270584 filed in the Japan Patent Office on Dec. 9, 2011, the entire content of which is hereby incorporated by reference.

BACKGROUND

The present application relates to a light detection apparatus and a light detection method that detect light emitted from a specimen using a photo-diode.

In the field of medical treatment, scientific research, and the like, detection of light emitted from a specimen is often performed. For example, by irradiating a specimen with excitation light to measure fluorescence or phosphorescence generated in the specimen, it is possible to detect that the specimen contains material that generates such light.

For the detection of light, a photo-diode is generally used. The photo-diode is capable of outputting an amount of light as a current. However, in the case where highly accurate measurement is necessary, noise is problematic. Increasing a light reception time period (exposure time period) of the photo-diode can make a signal-to-noise ratio (SNR) larger, but there is a problem that a measurement time period increases. This is remarkable especially in the case where weak light is measured by long-time exposure, for example, in fluorescence measurement.

In view of this, Japanese Patent Application Laid-open No. 2009-128648 (hereinafter, referred to as Patent Document 1) describes a microscope observation system. The microscope observation system is capable of measuring a noise level of an image sensor in a light-shielding state before measurement to adjust an exposure time period based on the noise level. With the microscope observation system, it is possible to reduce the influence on the measurement result by setting the exposure time period so that noise is within a certain range.

SUMMARY

As the exposure time period becomes longer, the SNR becomes larger. However, a rate of increase of the SNR gradually decreases. Therefore, with a certain noise level being a reference, there is a fear that the measurement time period may become too long. Thus, in the technique as described in Patent Document 1, it is difficult to optimize the exposure time period so that the SNR has a necessary and sufficient value (allowable minimum value).

In view of the above-mentioned circumstances, it is desirable to provide a light detection apparatus and a light detection method that are capable of optimizing an exposure time period.

According to an embodiment of the present application, there is provided a light detection apparatus includes an image sensor, a signal obtaining unit, an exposure-time-period determination unit, and an exposure controller.

The signal obtaining unit is configured to obtain a first dark current being a dark current of the image sensor in a first exposure time period, and a second dark current being a dark current of the image sensor in a second exposure time period.

The exposure-time-period determination unit is configured to determine an optimal exposure time period of the image sensor based on the first dark current and the second dark current.

The exposure controller is configured to control the image sensor to be exposed to light for the optimal exposure time period.

With this configuration, the signal obtaining unit obtains two dark currents in the different exposure time periods, and hence it is possible to obtain fluctuation of the dark current with respect to the exposure time period. Thus, based on the fluctuation, fluctuation of a signal-to-noise ratio (SNR) with respect to the exposure time period can be obtained. Further, the exposure-time-period determination unit determines the optimal exposure time period by comparing the SNR with respect to the exposure time period with a necessary SNR set in advance, and the exposure controller controls the image sensor to be exposed to light for the optimal exposure time period. Thus, the image sensor can be exposed to light for the optimal exposure time period.

The signal obtaining unit may be configured to further obtain a measurement current being an output of the image sensor that receives reference light.

The exposure-time-period determination unit may be configured to determine the optimal exposure time period based on the measurement current in addition to the first dark current and the second dark current.

With this configuration, when determining the fluctuation of the SNR with respect to the exposure time period, the exposure-time-period determination unit is capable of determining the fluctuation of the SNR with respect to the exposure time period more accurately, using the actually measured measurement current.

The exposure controller may be configured to determine, when the optimal exposure time period exceeds a threshold, that a life span of the image sensor has expired.

The image sensor increases in noise level due to aged deterioration, and hence needs to be replaced in view of the period of use. The light detection apparatus according to the embodiment of the present application determines the optimal exposure time period based on the fluctuation of the SNR with respect to the exposure time period, and hence the light detection apparatus is capable of determining, when the optimal exposure time period is too long, that the life span of the image sensor has expired.

The exposure-time-period determination unit may be configured to calculate a read-out noise of the image sensor based on the first dark current and the second dark current and to use the read-out noise for determination of the optimal exposure time period.

The image sensor has a read-out noise generated upon read-out. By obtaining the dark currents in the plurality of exposure time periods, the light detection apparatus according to the embodiment of the present application is capable of determining the read-out noise and using the read-out noise for determination of the optimal exposure time period.

According to another embodiment of the present application, there is provided a light detection apparatus including an excitation light source, an image sensor, a signal obtaining unit, an exposure-time-period determination unit, and an exposure controller.

The excitation light source is configured to irradiate a measurement object with excitation light.

Into the image sensor, one of fluorescence and phosphorescence emitted from the measurement object due to the excitation light.

The signal obtaining unit is configured to obtain a first dark current being a dark current of the image sensor in a first exposure time period, and a second dark current being a dark current of the image sensor in a second exposure time period.

The exposure-time-period determination unit is configured to determine an optimal exposure time period of the image sensor based on the first dark current and the second dark current.

The exposure controller is configured to control the image sensor to be exposed to light for the optimal exposure time period.

According to still another embodiment of the present application, there is provided a light detection method. In this light detection method, a first dark current being a dark current of an image sensor in a first exposure time period, and a second dark current being a dark current of the image sensor in a second exposure time period are obtained by a signal obtaining unit.

An optimal exposure time period of the image sensor is determined by an exposure-time-period determination unit based on the first dark current and the second dark current.

The image sensor is controlled by an exposure controller to be exposed to light for the optimal exposure time period.

As described above, according to the embodiments of the present application, it is possible to provide a light detection apparatus and a light detection method that are capable of optimizing an exposure time period.

These and other objects, features and advantages of the present disclosure will become more apparent in light of the following detailed description of best mode embodiments thereof, as illustrated in the accompanying drawings.

Additional features and advantages are described herein, and will be apparent from the following Detailed Description and the figures.

DETAILED DESCRIPTION

A light detection apparatus according to an embodiment of the present application will be described. Although the light detection apparatus according to this embodiment can be used as various apparatuses using an image sensor, herein, a case where the light detection apparatus is used as a fluorescence microscope will be described as an example.

[Configuration of Fluorescence Microscope]

Figure 1:
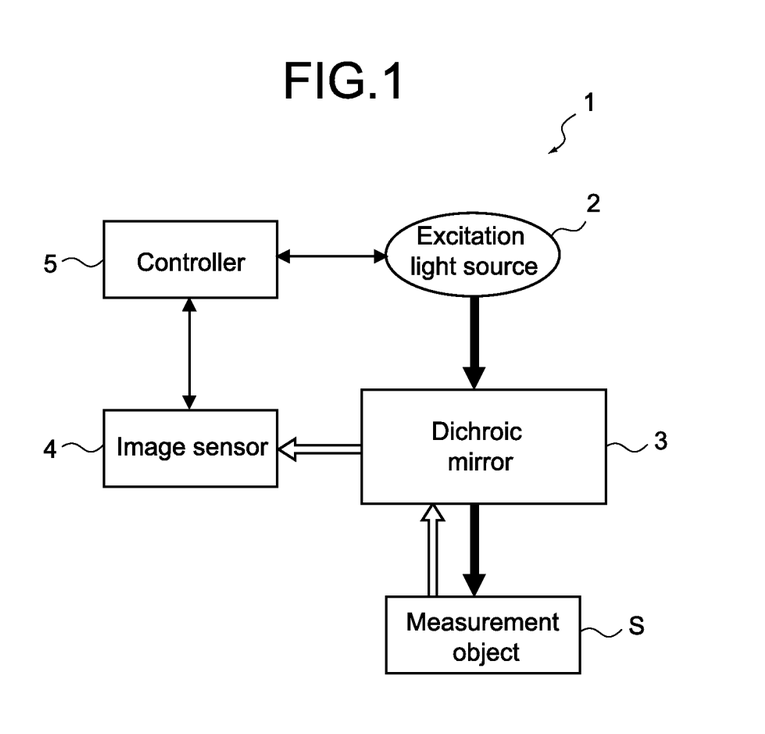
FIG. 1 is a schematic diagram showing a configuration of a fluorescence microscope according to an embodiment of the present application.

FIG. 1 is a schematic diagram showing a fluorescence microscope 1. As shown in the figure, the fluorescence microscope 1 includes an excitation light source 2, a dichroic mirror 3, an image sensor 4, and a controller 5. Note that, it is assumed that a measurement object S is set in the fluorescence microscope 1.

In the fluorescence microscope 1, fluorescence generated in the measurement object S when the measurement object S is irradiated with excitation light is a measurement target. In FIG. 1, excitation light is shown by a bold black arrow and fluorescence is shown by a white arrow.

The excitation light source 2 emits excitation light. Any excitation light source can be used depending on a wavelength of excitation light as the excitation light source 2. Between the excitation light source 2 and the dichroic mirror 3, a filter that cuts light having an unnecessary wavelength, an optical system that converts an irradiation angle of excitation light, and the like may be provided.

The dichroic mirror 3 is a mirror that reflects light in a predetermined wavelength range and transmits light in a wavelength range other than the predetermined wavelength range. Herein, one that transmits light in a wavelength range of excitation light and reflects light in a wavelength range of fluorescence can be used.

The image sensor 4 detects fluorescence. The image sensor 4 only needs to include a built-in photo-diode and may have any image-sensor structure, for example, a charge coupled device (CCD) or a complementary metal oxide semiconductor (CMOS).

The controller 5 obtains an output of the image sensor 4 and controls the image sensor 4 and the excitation light source 2. The controller 5 may be incorporated in the fluorescence microscope 1 or may be an external device of a personal computer (PC) or the like. A specific configuration of the controller 5 will be described later.

Measurement of the measurement object S by the fluorescence microscope 1 is performed in the following manner. The excitation light emitted from the excitation light source 2 passes through the dichroic mirror 3 and then the measurement object S is irradiated with the excitation light. In the measurement object S, fluorescence is generated due to the excitation light. The fluorescence is reflected by the dichroic mirror 3 and inputs into the image sensor 4. In the image sensor 4, the exposure is continued for a predetermined exposure time period and an accumulated charge is outputted to the controller 5. In the controller 5, a fluorescence image is created.

Note that, in the case where weak light such as fluorescence and phosphorescence is a measurement target, in general, the exposure is continued for a relatively long time period (several tens of seconds or more). Therefore, due to the necessity of the long-time exposure in addition to weak light, the influence of noise in the image sensor on the measurement result is not small. The present application is effective especially in such a case where the light being the measurement target is weak.

[Configuration and Operation of Controller]

Figure 2:
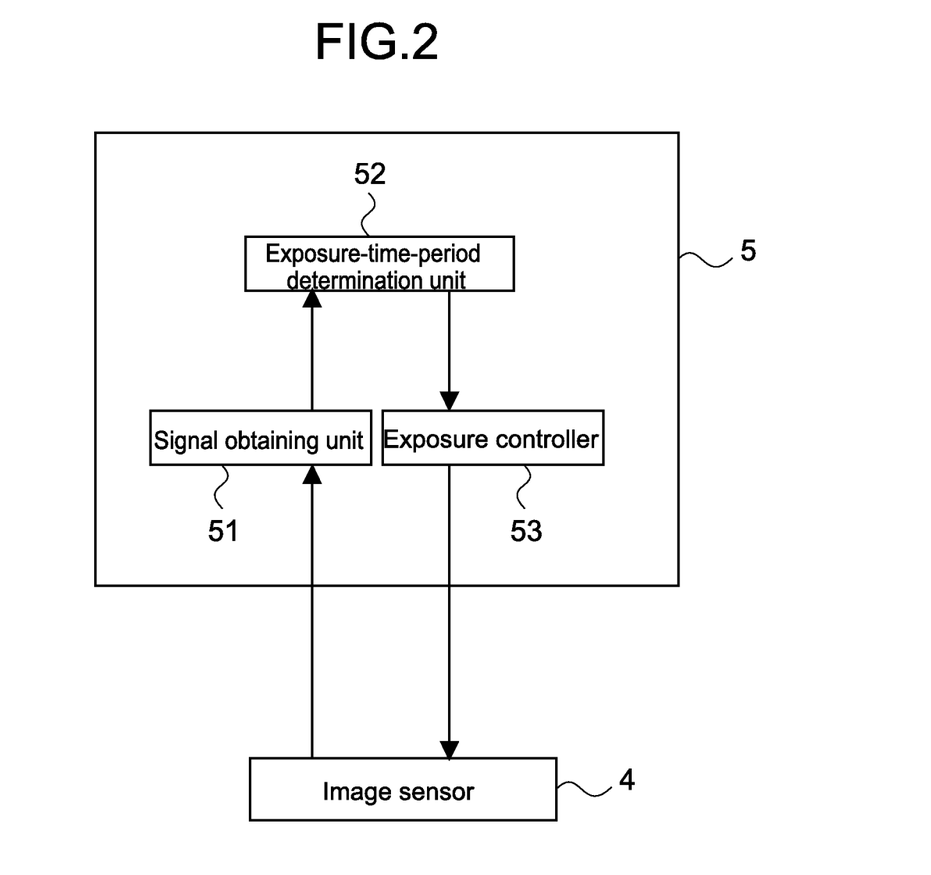
FIG. 2 is a schematic diagram showing a functional configuration of a controller of the fluorescence microscope.
Figure 3:
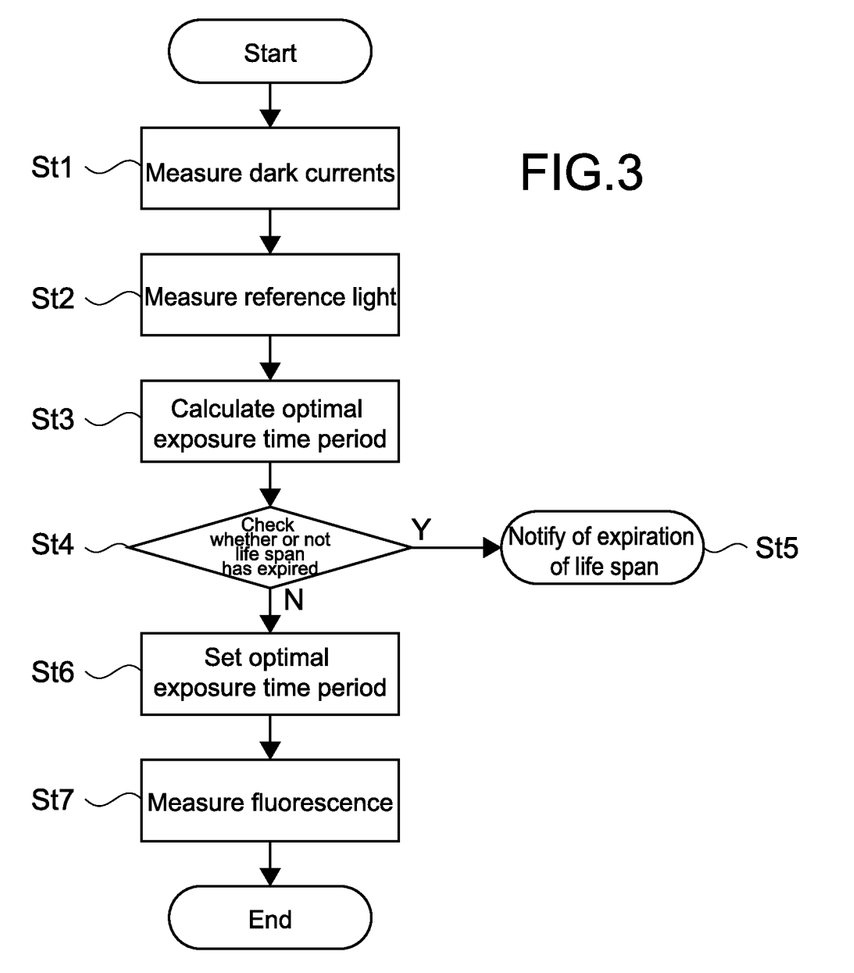
FIG. 3 is a flowchart showing an operation of the fluorescence microscope.

A configuration and an operation of the controller 5 will be described. FIG. 2 is a schematic diagram showing a functional configuration of the controller 5. As shown in the figure, the controller 5 includes a signal obtaining unit 51, an exposure-time-period determination unit 52, and an exposure controller 53. Those components are realized by the cooperation of hardware such as a processor and software read therein. Hereinafter, the configuration of the controller 5 will be described together with an operation of the fluorescence microscope 1. FIG. 3 is a flowchart showing the operation of the fluorescence microscope 1.

First, before the fluorescence measurement, a dark current of the image sensor 4 is measured (St1). This dark-current measurement may be performed before each fluorescence measurement or after a plurality of times of fluorescence measurement. Specifically, the image sensor 4 is energized in a state in which the image sensor 4 is shielded from light, and an accumulated charge after a predetermined period time has elapsed is obtained by the signal obtaining unit 51 as the dark current. A time period after the start of the energization of the image sensor 4 before the output of the charge is defined as an exposure time period.

Figure 4:
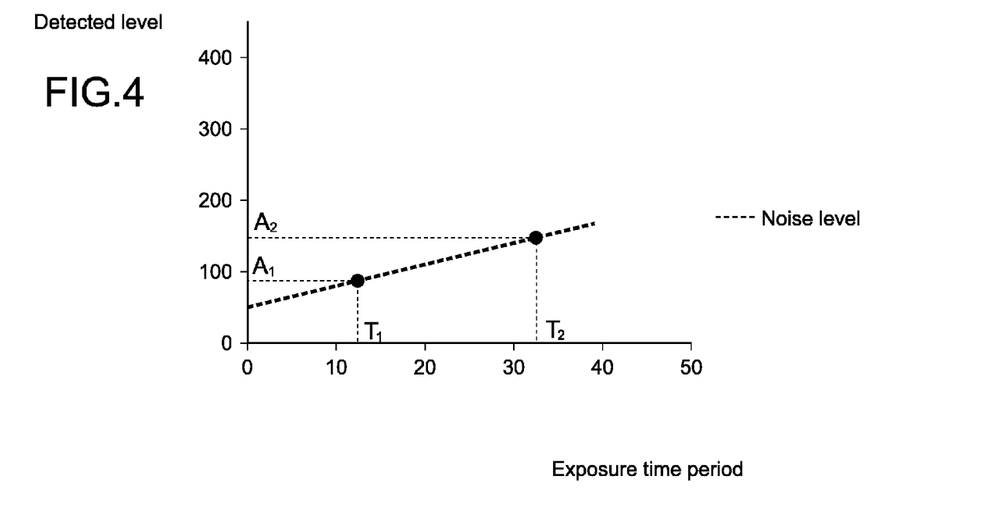
FIG. 4 is a graph showing a dark current of an image sensor of the fluorescence microscope.

FIG. 4 is a graph showing an example of the dark current of the image sensor 4. The dark current (noise level) is the output in the state in which the image sensor 4 is shielded from light, and hence is a noise component derived from the image sensor 4. The noise level in this graph increases proportionally to the exposure time period. That is because the dark current increases proportionally to the exposure time period. Further, the noise level in the graph has a certain value even at an exposure time period of 0. This value is a value of a read-out noise of the image sensor 4.

The signal obtaining unit 51 obtains dark currents (noise levels) in two exposure time periods (first exposure time period T1 and second exposure time period T2). The dark current in the first exposure time period T1 is referred to as a first dark current A1. Meanwhile, the dark current in the second exposure time period T2 is referred to as a second dark current A2. The signal obtaining unit 51 obtains the first dark current A1 and the second dark current A2, so that the graph of the noise level of FIG. 4 is obtained.

If the signal obtaining unit 51 obtains only a dark current in a certain exposure time period, the graph of the noise level of FIG. 4 is not obtained. That is because the line on graph does not pass through an origin at the exposure time period of 0 due to the read-out noise at the exposure time period of 0. The signal obtaining unit 51 outputs the first dark current A1 and the second dark current A2 to the exposure-time-period determination unit 52. Note that, the signal obtaining unit 51 may obtain dark currents in three or more exposure time periods.

Figure 5:
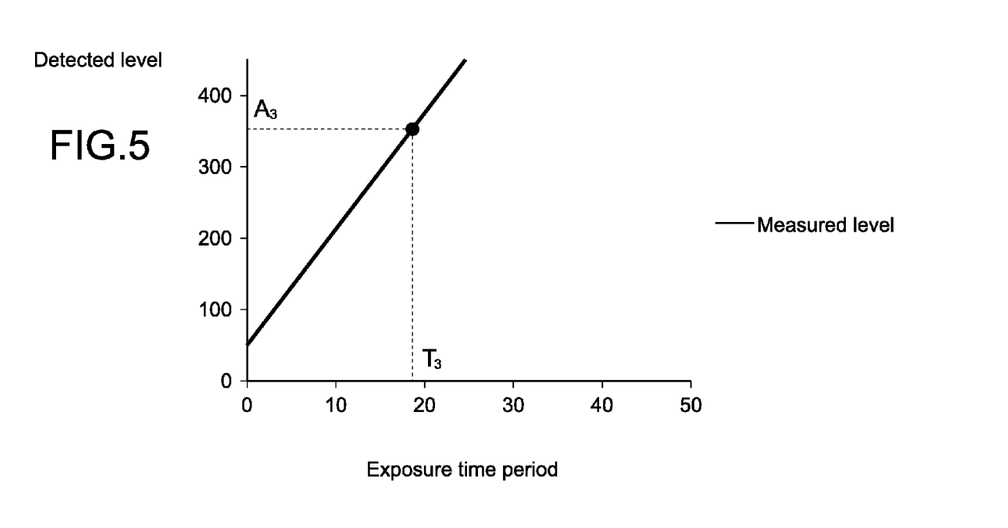
FIG. 5 is a graph showing a result of reference light measurement of the fluorescence microscope.

Next, reference light measurement (St2) is performed. FIG. 5 is a graph showing a result of the reference light measurement. The reference light measurement is performed with reference luminescent material containing a predetermined amount of fluorescent material being a measurement target instead of the measurement object S. In the graph of FIG. 5, the noise level shown in the FIG. 4 is added to a signal level (original signal level) generated by fluorescence from the reference luminescent material.

Figure 6:
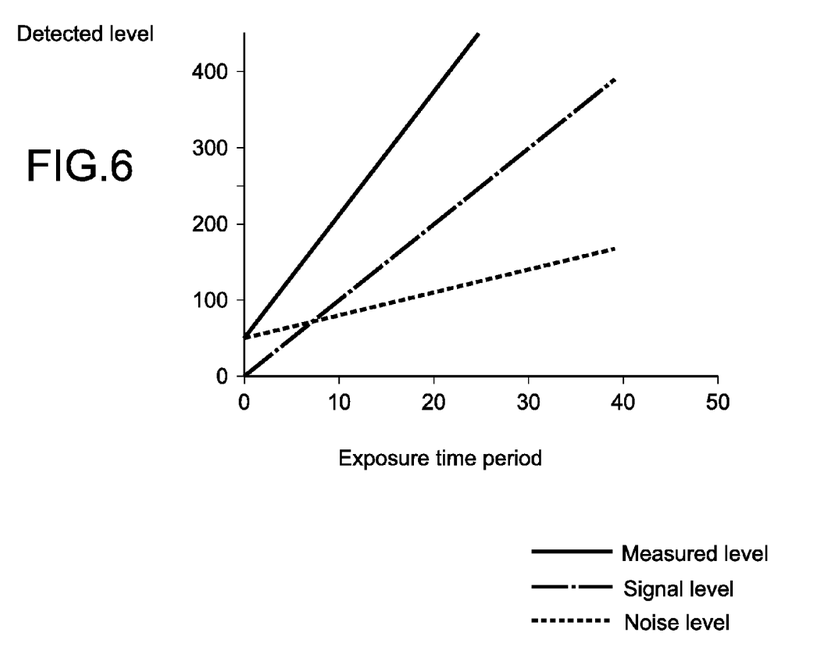
FIG. 6 is a graph showing a signal level of the image sensor of the fluorescence microscope.

Therefore, a difference between the measured level shown in the graph of FIG. 5 and the noise level shown in the graph of FIG. 4 is the original signal level without the noise component. FIG. 6 is a graph showing the original signal level. At the exposure time period of 0, fluorescence is not inputted into the image sensor 4, and hence the signal level is 0. Therefore, based on an output (referred to as measurement current A3) of the image sensor 4 in a certain exposure time period T3, the graph of FIG. 5 is obtained. That is because, at the exposure time period of 0, the value of the read-out noise (intercept of line on graph of FIG. 4) only needs to be set. The signal obtaining unit 51 outputs a result of the reference light measurement to the exposure-time-period determination unit 52.

Note that, the reference light measurement may not be performed. That is because the amount of fluorescence generated by the reference luminescent material is defined and hence the graph of FIG. 5 can be estimated. It should be noted that, when the reference light measurement is performed, it is possible to more optimally determine an optimal exposure time period, which will be described later.

Next, a determination of the optimal exposure time period (St3) is performed. The exposure-time-period determination unit 52 determines the optimal exposure time period based on the first dark current A1, the second dark current A2, and the measurement current A3 that are supplied from the signal obtaining unit 51. Otherwise, when the reference light measurement is not performed, the exposure-time-period determination unit 52 determines the optimal exposure time period based on the first dark current A1, the second dark current A2, and the estimated graph (corresponding to FIG. 5).

Figure 7A:
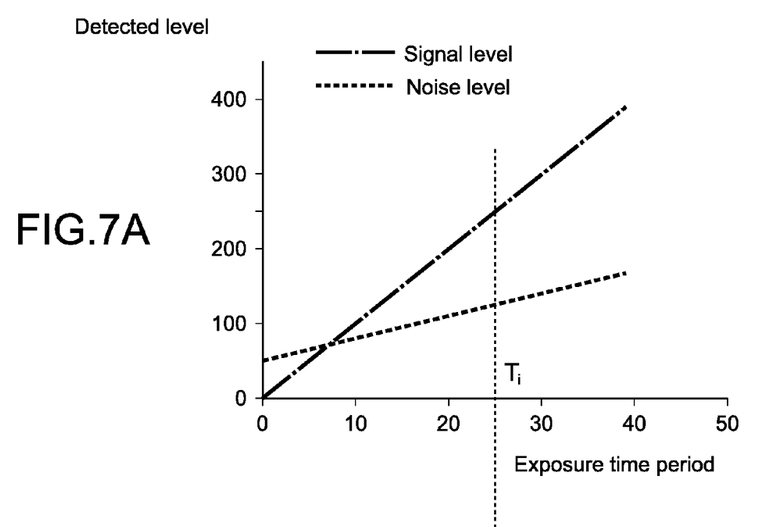
FIGS. 7A and 7B are graphs each showing a determination method for an optimal exposure time period of the fluorescence microscope.
Figure 7B:
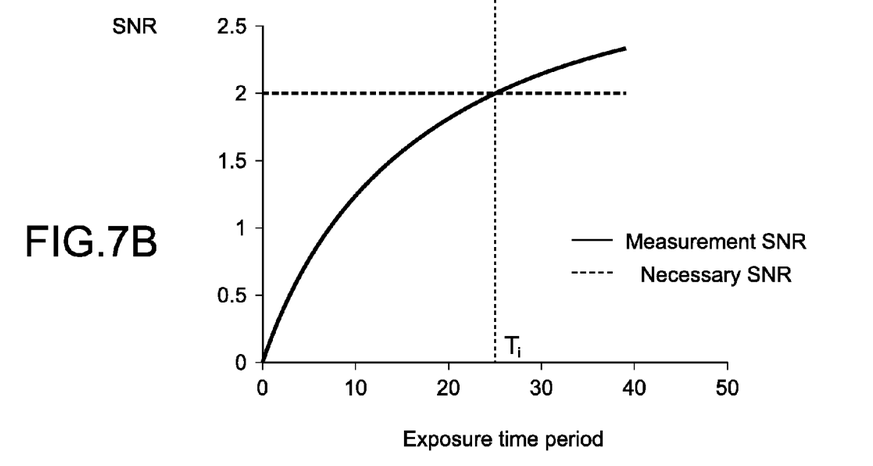

FIGS. 7A and 7B are graphs each showing a determination method for the optimal exposure time period. As shown in FIG. 7A, the exposure-time-period determination unit 52 generates a graph of the noise level based on the first dark current A1 and the second dark current A2, and generates a graph of the signal level based on the measurement current A3 or by estimation. Subsequently, the exposure-time-period determination unit 52 generates a graph of the SNR (referred to as measurement SNR) shown in FIG. 7B by dividing the signal level by the noise level.

The exposure-time-period determination unit 52 determines such an exposure time period that the measurement SNR corresponds to a necessary and sufficient SNR (referred to as necessary SNR) set in advance, as an optimal exposure time period Ti. The exposure-time-period determination unit 52 outputs the determined optimal exposure time period Ti to the exposure controller 53.

Here, checking of a life span of the image sensor 4 (St4) may be performed. The image sensor 4 may increase in noise level due to aged deterioration. Therefore, when the optimal exposure time period Ti exceeds a predetermined threshold, the exposure controller 53 may determine that the life span of the image sensor 4 has expired and stop the fluorescence measurement. The exposure controller 53 may notify (St5) a user of the life span of the image sensor 4 having elapsed by, for example, displaying a message on a display.

When the checking of the life span of the image sensor 4 is not performed or the image sensor 4 is in a good state, setting of the optimal exposure time period (St6) is performed. The exposure controller 53 sets the optimal exposure time period Ti determined in the exposure-time-period determination unit 52, as an exposure time period for the fluorescence measurement.

Subsequently, the fluorescence measurement (St7) is performed. In the fluorescence measurement, the measurement object S is set in the fluorescence microscope 1 and fluorescence of the measurement object S is measured as described above. At this time, the exposure controller 53 controls the image sensor 4 so that the exposure time period of the image sensor 4 is the optimal exposure time period Ti.

In this manner, the fluorescence measurement is performed. The exposure time period is set to be such an optimal exposure time period that the SNR is necessary and sufficient. Therefore, it is possible to shorten the measurement time period while ensuring the measurement accuracy, which is advantageous.

The present application is not limited only to the above-mentioned embodiment and can be changed without departing from the gist of the present application.

Although, in the above-mentioned embodiment, the light detection apparatus is used as the fluorescence microscope, the light detection apparatus is not limited thereto. The present application is applicable to any apparatus that detects weak light such as fluorescence and phosphorescence using an image sensor.

It should be noted that the present application may also take the following configurations.
(1) A light detection apparatus, including:
   an image sensor;
   a signal obtaining unit configured to obtain
      a first dark current being a dark current of the image sensor in a first exposure time period, and
      a second dark current being a dark current of the image sensor in a second exposure time period;
   an exposure-time-period determination unit configured to determine an optimal exposure time period of the image sensor based on the first dark current and the second dark current; and
   an exposure controller configured to control the image sensor to be exposed to light for the optimal exposure time period.
(2) The light detection apparatus according to (1), in which
   the signal obtaining unit is configured to further obtain a measurement current being an output of the image sensor that receives reference light, and
   the exposure-time-period determination unit is configured to determine the optimal exposure time period based on the measurement current in addition to the first dark current and the second dark current.
(3) The light detection apparatus according to (1) or (2), in which
   the exposure controller is configured to determine, when the optimal exposure time period exceeds a threshold, that a life span of the image sensor has expired.
(4) The light detection apparatus according to any one of (1) to (3), in which
   the exposure-time-period determination unit is configured to calculate a read-out noise of the image sensor based on the first dark current and the second dark current and to use the read-out noise for determination of the optimal exposure time period.
(5) A light detection apparatus, including:
   an excitation light source configured to irradiate a measurement object with excitation light;
   an image sensor into which one of fluorescence and phosphorescence emitted from the measurement object due to the excitation light;
   a signal obtaining unit configured to obtain
      a first dark current being a dark current of the image sensor in a first exposure time period, and
      a second dark current being a dark current of the image sensor in a second exposure time period;
   an exposure-time-period determination unit configured to determine an optimal exposure time period of the image sensor based on the first dark current and the second dark current; and
   an exposure controller configured to control the image sensor to be exposed to light for the optimal exposure time period.
(6) A light detection method, including:
   obtaining, by a signal obtaining unit,
      a first dark current being a dark current of the image sensor in a first exposure time period, and
      a second dark current being a dark current of the image sensor in a second exposure time period;
   determining, by an exposure-time-period determination unit, configured to determine an optimal exposure time period of the image sensor based on the first dark current and the second dark current; and
   controlling, by an exposure controller, the image sensor to be exposed to light for the optimal exposure time period.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A light detection apparatus, comprising:
   an image sensor;
   a signal obtaining unit configured to obtain
      a first dark current being a dark current of the image sensor in a first exposure time period, and
      a second dark current being a dark current of the image sensor in a second exposure time period;
   an exposure-time-period determination unit configured to determine a noise level based on the first dark current and the second dark current and a signal level based on a measurement current or by estimation, and to compute an optimal exposure time period based on the noise level and the signal level; and
   an exposure controller configured to control the image sensor to be exposed to light for the optimal exposure time period.

2. The light detection apparatus according to claim 1, wherein
   the signal obtaining unit is configured to further obtain the measurement current as an output of the image sensor that receives reference light, and
   the exposure-time-period determination unit is configured to determine the optimal exposure time period based on the measurement current obtained from the image sensor.

3. The light detection apparatus according to claim 1, wherein
   the exposure controller is configured to determine, when the optimal exposure time period exceeds a threshold, that a life span of the image sensor has expired.

4. The light detection apparatus according to claim 1, wherein
   the exposure-time-period determination unit is configured to calculate a read-out noise of the image sensor based on the first dark current and the second dark current and to use the read-out noise for determination of the optimal exposure time period.

5. The light detection apparatus according to claim 1, wherein the exposure-time-period determination unit computes the optimal exposure time by dividing the signal level by the noise level.

6. A light detection apparatus, comprising:
   an excitation light source configured to irradiate a measurement object with excitation light;
   an image sensor into which one of fluorescence and phosphorescence emitted from the measurement object due to the excitation light;
   a signal obtaining unit configured to obtain
      a first dark current being a dark current of the image sensor in a first exposure time period, and
      a second dark current being a dark current of the image sensor in a second exposure time period;
   an exposure-time-period determination unit configured to determine a noise level based on the first dark current and the second dark current and a signal level based on a measurement current or by estimation, and to compute an optimal exposure time period based on the noise level and the signal level; and an exposure controller configured to control the image sensor to be exposed to light for the optimal exposure time period.

7. A light detection method, comprising:

obtaining, by a signal obtaining unit,
- a first dark current being a dark current of the image sensor in a first exposure time period, and
- a second dark current being a dark current of the image sensor in a second exposure time period;

determining, by an exposure-time-period determination unit, a noise level based on the first dark current and the second dark current and a signal level based on a measurement current or by estimation;

computing, by the exposure-time-period determination unit, an optimal exposure time period based on the noise level and the signal level; and controlling, by an exposure controller, the image sensor to be exposed to light for the optimal exposure time period.

* * * * *